US010131860B2

(12) United States Patent
Iba et al.

(10) Patent No.: US 10,131,860 B2
(45) Date of Patent: Nov. 20, 2018

(54) DIALKYL POLYSULFIDE, PROCESS FOR PREPARING DIALKYL POLYSULFIDE, EXTREME PRESSURE ADDITIVE, AND LUBRICATING FLUID COMPOSITION

(71) Applicant: DIC Corporation, Tokyo (JP)

(72) Inventors: Takafumi Iba, Ichihara (JP); Hiroshi Sakata, Ichihara (JP)

(73) Assignee: DIC Corporation, Tokyo (JP)

( * ) Notice: Subject to any disclaimer, the term of this patent is extended or adjusted under 35 U.S.C. 154(b) by 50 days.

(21) Appl. No.: 14/891,372

(22) PCT Filed: May 15, 2014

(86) PCT No.: PCT/JP2014/062935
§ 371 (c)(1),
(2) Date: Nov. 16, 2015

(87) PCT Pub. No.: WO2014/188948
PCT Pub. Date: Nov. 27, 2014

(65) Prior Publication Data
US 2016/0097016 A1    Apr. 7, 2016

(30) Foreign Application Priority Data
May 20, 2013 (JP) .................. 2013-106095

(51) Int. Cl.
| *C10M 135/22* | (2006.01) |
| *C07C 321/14* | (2006.01) |
| *C07C 319/16* | (2006.01) |
| *C10M 169/04* | (2006.01) |

(52) U.S. Cl.
CPC ......... *C10M 135/22* (2013.01); *C07C 319/16* (2013.01); *C07C 321/14* (2013.01); *C10M 169/04* (2013.01); *C10M 2219/082* (2013.01); *C10N 2230/06* (2013.01); *C10N 2230/12* (2013.01); *C10N 2260/10* (2013.01); *C10N 2270/00* (2013.01)

(58) Field of Classification Search
CPC ...................... C10M 135/22; C10M 2219/082
USPC ......................................................... 508/569
See application file for complete search history.

(56) References Cited

U.S. PATENT DOCUMENTS

| 4,119,549 A * | 10/1978 | Davis .................... C07G 17/004 508/324 |
| 4,119,550 A * | 10/1978 | Davis .................... C07G 17/004 508/324 |
| 4,191,659 A * | 3/1980 | Davis .................... C07G 17/004 252/406 |
| 4,344,854 A * | 8/1982 | Davis .................... C07G 17/004 508/324 |
| 4,584,113 A | 4/1986 | Walsh |
| 5,091,112 A * | 2/1992 | Perozzi ................. C07C 319/22 252/387 |
| 5,091,593 A | 2/1992 | Lindstrom et al. |
| 5,135,670 A * | 8/1992 | Johnson ............... C07G 17/004 508/324 |
| 5,174,922 A | 12/1992 | Perozzi et al. |
| 5,208,382 A * | 5/1993 | Perozzi ................. C07C 319/28 208/226 |
| 5,242,672 A * | 9/1993 | Yen ....................... C07C 319/28 166/312 |
| 5,250,737 A * | 10/1993 | Ozbalik ................ C07C 319/24 568/21 |
| 6,362,136 B1 * | 3/2002 | Richardson .......... C10M 141/12 508/186 |
| 6,689,723 B2 * | 2/2004 | Sullivan ............... C10M 135/22 508/185 |
| 9,562,006 B2 * | 2/2017 | Fremy ................... C07C 319/24 |

FOREIGN PATENT DOCUMENTS

| EP | 0554011 A2 | 8/1993 |
| JP | 59-10559 A | 1/1984 |
| JP | 62-500590 A | 3/1987 |
| JP | 03-034965 A | 2/1991 |
| JP | 05-247675 A | 9/1993 |
| JP | 05-286925 A | 11/1993 |
| JP | 2012-077078 A | 4/2012 |

OTHER PUBLICATIONS

W. Davey et al., "The Extreme-Pressure Lubricating Properties of Some Sulphides and Disulphides, in Mineral Oil, as Assessed by the Four-Ball Machine," Wear, vol. 1, 1957/58, pp. 291-304.
D. N. Harpp et al., "Desulfurization of Organic Trisuifides by Tris(dialkylamino)phosphines. Mechanistic Aspects," The Journal of Organic Chemistry, 1980, vol. 45, pp. 5155-5160.
D. N. Harpp et al., "Reaction of Trialkyl Phosphites with Organic Trisulfides. Synthetic and Mechanistic Aspects," The Journal of Organic Chemistry, vol. 44, No. 23, 1979, pp. 4140-4144.
N. Iranpoor et al., "Heteroaromatic azo compounds as efficient and recyclable reagents for direct conversion of aliphatic alcohols into symmetrical disulfides," Tetrahedron Letters, vol. 53, 2012, pp. 6913-6915.

(Continued)

*Primary Examiner* — Ellen M McAvoy
(74) *Attorney, Agent, or Firm* — Locke Lord LLP

(57) ABSTRACT

The present invention provides a dialkyl polysulfide which can be suitably used as an extreme pressure additive that can be added to a lubricant in a wide range of amounts, that enables effective formation of a film of a metal sulfide on a metal surface, and that is less likely to cause corrosion of the metal surface. In particular, provided is a dialkyl polysulfide containing compounds represented by General Formula (1) (where $R^1$ and $R^2$ each represent an alkyl group, and n is an integer from 1 to 6), wherein the total content of a compound in which n in General Formula (1) is 2 and a compound in which n in General Formula (1) is 3 is in the range of 80 to 100 mass % relative to the entire amount of the compounds represented by General Formula (1).

18 Claims, No Drawings

(56) References Cited

OTHER PUBLICATIONS

W. de Graaf et al., "Low-temperature addition of hydrogen polysulfides to olefins: formation of 2,2'-dialkyl polysulfides from alk-1-enes and cyclic (poly)sulfides and polymeric organic sulfur compounds from a,w-dienes," Journal of the Chemical Society Perkin Transactions, 1, 1995, pp. 635-640.

J. Choi et al., "A Convenient One-Pot Synthesis of Disulfides from Thioacetates via Nickel Boride Catalyzed Methanolysis and Disproportionation," Synlett, vol. 10, 1995, pp. 1073-1074.

International Search Report and Written Opinion dated Jul. 22, 2014, issued for PCT/JP2014/062935.

* cited by examiner

DIALKYL POLYSULFIDE, PROCESS FOR PREPARING DIALKYL POLYSULFIDE, EXTREME PRESSURE ADDITIVE, AND LUBRICATING FLUID COMPOSITION

TECHNICAL FIELD

The present invention relates to a dialkyl polysulfide which can be suitably used as an extreme pressure additive that can be added to a lubricant in a wide range of amounts, that enables effective formation of a film of a metal sulfide on a metal surface, and that is less likely to cause corrosion of the metal surface; and the present invention also relates to a method for producing the dialkyl polysulfide. The present invention further relates to an extreme pressure additive containing such a dialkyl polysulfide and a lubricating fluid composition containing this extreme pressure additive.

BACKGROUND ART

An extreme pressure additive has been typically used in lubricating fluid compositions, such as a cutting oil, a plastic working lubricant, a gear oil, a slideway oil, and grease, in order to reduce the friction and abrasion of metals and to prevent seizure. Examples of the extreme pressure additive include chlorine-containing organic compounds, such as chlorinated paraffin and chlorinated fatty acid esters, and sulfur-containing organic compounds including sulfurized fats and sulfurized olefins, such as dialkyl polysulfide; among these, dialkyl polysulfide has been widely used because it enables an extreme pressure additive to have a high sulfur content, has high solubility in a base oil, and enables a larger amount of sulfur to be added to a base oil.

Examples of dialkyl sulfide include dialkyl monosulfides and dialkyl polysulfides such as dialkyl disulfide, dialkyl trisulfide, and dialkyl tetrasulfide. A known example of such dialkyl polysulfides is a dialkyl polysulfide containing unbranched alkyl groups each having 4 to 22 carbon atoms (e.g., see Patent Literature 1). According to Patent Literature 1, this dialkyl polysulfide can be produced by the reaction of an olefin having 4 to 22 carbon atoms and unbranched terminals with sulfur and a hydrogen sulfide in the presence of a catalyst, and the produced dialkyl polysulfide is a mixture of dialkyl polysulfides each having approximately 1 to 6 sulfur atoms and generally used in the form of this produced mixture.

In dialkyl polysulfide, dialkyl monosulfide generally has a bad reactivity with metal and is unable to efficiently form a film of a metal sulfide on a metal surface. Thus, in use of a mixture of dialkyl polysulfides with the large dialkyl monosulfide content, the amount thereof in a lubricating fluid needs to be large in order to form a film of a metal sulfide. Meanwhile, among dialkyl polysulfides, a dialkyl polysulfide containing more sulfur atoms, such as dialkyl tetrasulfide, has a good reactivity with metal and therefore enables efficient formation of a film of a metal sulfide. An increase in the amount of such a dialkyl polysulfide containing more sulfur atoms, however, causes corrosion of a metal surface because of its high reactivity. Hence, in use of a mixture containing both dialkyl monosulfide and dialkyl tetrasulfide in large concentrations, the amount thereof in a lubricating fluid is limited within the narrow range that enables efficient formation of a film of a metal sulfide and that does not cause corrosion.

CITATION LIST

Patent Literature

PTL 1: Japanese Unexamined Patent Application Publication No. 11-071343

SUMMARY OF INVENTION

Technical Problem

It is an object of the present invention to provide a dialkyl polysulfide which can be suitably used as an extreme pressure additive that can be added to a lubricating fluid in a wide range of amounts, that enables effective formation of a film of a metal sulfide on a metal surface, and that is less likely to cause corrosion of the metal surface and to provide a method for producing the dialkyl polysulfide. It is another object of the present invention to provide an extreme pressure additive containing such a dialkyl polysulfide and a lubricating fluid composition containing this extreme pressure additive.

Solution to Problem

The inventors have intensively studied to achieve the above-mentioned objects and found the following, thereby accomplishing the present invention: in a mixture of dialkyl polysulfides each having a specific dialkyl group, dialkyl polysulfides in which the dialkyl disulfide content and the dialkyl trisulfide content are within a specific range enable efficient formation of a film of a metal sulfide on a metal surface, are less likely to cause the corrosion of a metal surface, and can properly serve as an extreme pressure additive, when it is added to a lubricant in a variety of amounts.

In particular, the present invention provides a dialkyl polysulfide containing compounds represented by General Formula (1).

[Chem. 1]

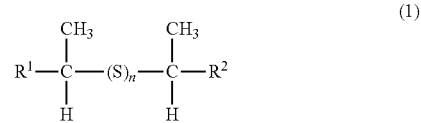

(where $R^1$ and $R^2$ each represent an alkyl group, and n is an integer from 1 to 6), wherein
the total content of a compound in which n in General Formula (1) is 2 and a compound in which n in General Formula (1) is 3 is in the range of 80 to 100 mass % relative to the entire amount of the compounds represented by General Formula (1).

The present invention also provides a method for producing dialkyl polysulfide, the method including a first process in which a 1-olefin compound (a) having a linear end is allowed to react with sulfur in the presence of a hydrogen sulfide to obtain a dialkyl polysulfide (A) and a second process in which the dialkyl polysulfide compound (A) is allowed to react with a sulfide of an alkali metal to reduce the number of sulfur atoms contained in the dialkyl polysulfide (A).

The present invention also provides an extreme pressure additive containing the above-mentioned dialkyl polysulfide.

The present invention also provides a lubricating fluid composition containing the above-mentioned extreme pressure additive.

Advantageous Effects of Invention

The dialkyl polysulfide of the present invention is useful as a high-performance extreme pressure additive which is less likely to causes the corrosion of a metal surface when it is added to a lubricating fluid in a large amount, enables effective formation of a film of a metal sulfide on a metal surface when it is added in a small amount, and can be used in a wide range of amounts. In addition, the production method of the present invention enables efficient production of the dialkyl polysulfide of the present invention.

DESCRIPTION OF EMBODIMENTS

The dialkyl polysulfide of the present invention contains compounds represented by General Formula (1).

[Chem. 2]

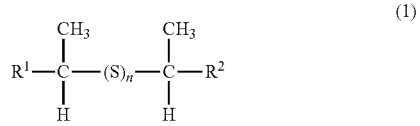

(1)

(where $R^1$ and $R^2$ each represent an alkyl group, and n is an integer from 1 to 6)

The total amount of a compound in which n in General Formula (1) is 2 and a compound in which n in General Formula (1) is 3 is in the range of 80 to 100 mass % relative to the entire amount of the compounds represented by General Formula (1).

In the dialkyl polysulfide of the present invention, the total amount of a compound in which n in General Formula (1) is 2 and a compound in which n in General Formula (1) is 3 is in the range of 80 to 100 mass % relative to the entire amount of the compounds represented by General Formula (1). In the case where such an amount is less than 80 mass %, dialkyl monosulfide having a low reactivity with metal is generated, or the amount of dialkyl tetrasulfide that is highly corrosive to a metal surface is large; hence, such content is not preferred. The amount is preferably in the range of 85 to 100 mass %, more preferably 85 to 95 mass %, and further preferably 90 to 95 mass % because it enables the dialkyl polysulfide of the present invention to be used in a wide range of amounts, to be less likely to corrode a metal surface, to effectively form a film of a metal sulfide on a metal surface even in use in a small amount, and to be easily obtained.

Examples of $R^1$ and $R^2$ in General Formula (1) include linear alkyl groups and branched alkyl groups. Examples of the linear alkyl groups include n-butane, n-pentane, n-octane, n-decane, n-dodecane, n-hexadecane, n-octadecane, and mixtures thereof. Examples of the branched alkyl groups include 3-methylpentane, 4-methylheptane, 5-methylundecane, and 3,6-dimethylhexandecane.

In particular, each of $R^1$ and $R^2$ in General Formula (1) is preferably a linear alkyl group having 4 to 20 carbon atoms, more preferably a linear alkyl group having 6 to 18 carbon atoms, and further preferably a linear alkyl group having 6 to 12 carbon atoms because it enables maintenance of the high sulfur content, good formation of a metal sulfide film on a metal surface, and a reduction in low molecular weight mercaptans that cause odor.

The active sulfur content in the dialkyl polysulfide of the present invention is preferably in the range of 0.1 to 30 mass %, and more preferably 0.5 to 20 mass % relative to the total sulfur content because it enables production of dialkyl polysulfide that can effectively form a film of a metal sulfide on a metal surface and that is less likely to corrode a metal surface. The active sulfur content can be measured in accordance with ASTM-D1662 in the present invention.

The 50% pyrolysis temperature of the dialkyl polysulfide of the present invention is, for example, from 200 to 300° C. This pyrolysis temperature is increased in proportion to an increase in the chain length of an alkyl group of each of $R^1$ and $R^2$ in General Formula (1). Mixing dialkyl polysulfides having a difference in the chain length of an alkyl group therefore enables production of dialkyl polysulfide (mixture) having a predetermined pyrolysis temperature.

The dialkyl polysulfide of the present invention can be properly produced by the production method of the present invention including, for instance, the following processes:

First Process: a process in which a 1-olefin compound (a) having a linear end is allowed to react with sulfur in the presence of a hydrogen sulfide to produce a dialkyl polysulfide (A) and Second Process: the dialkyl polysulfide compound (A) is allowed to react with a sulfide of an alkali metal to reduce the number of sulfur atoms contained in the dialkyl polysulfide (A).

Each of the processes will now be described in detail.

The olefin compound (a) used in the first process is a 1-olefin having a linear end. Examples of the olefin compound (a) include linear 1-olefin and branched 1-olefin having a branched part that is not at an end thereof. Examples of the linear 1-olefin include 1-butene, 1-pentene, 1-hexene, 1-octene, 1-decene, 1-dodecene, 1-tetradecene, 1-hexadecene, 1-octadecene, 1-eicosene, and mixtures thereof.

Examples of the branched 1-olefin having a branched part that is not at an end thereof include 3-methylpentene, 4-methylheptene, 5-methylundecene, 3,6-dimethylhexandecene, and mixtures thereof.

In particular, the olefin compound (a) used in the present invention is preferably the linear 1-olefin because it can be easily industrially obtained and the reaction thereof with sulfur is easily promoted. The linear 1-olefin is preferably an olefin compound having 6 to 22 carbon atoms, more preferably an olefin compound having 8 to 20 carbon atoms, and further preferably an olefin compound having 8 to 14 carbon atoms because each of them has a low pour point and can stay in a fluid state at normal temperature.

The sulfur can be in any form and may be, for example, in the solid state of a blob, a flake, or powder or in the melt (fluid) state. In particular, melted sulfur is preferred for the reason that it can make a feeding operation easy in large-scale production.

The hydrogen sulfide (a3) is not particularly limited; it is preferred that a material having a purity of not less than 99 mol % be used in order to allow the dialkyl polysulfide of the present invention to have high purity.

In the first process, when the olefin compound (a) is allowed to react with sulfur in the presence of a hydrogen sulfide, the reaction is preferably carried out in the presence of a basic compound (basic catalyst) because it enables efficient and easy production of the dialkyl polysulfide (A). Examples of the basic catalyst include, but not limited to, alkali metal hydroxides such as sodium hydroxide and potassium hydroxide and amine compounds such as aliphatic amine and aromatic amine. Examples of the amine compounds include butylamine, dibutylamine, tributylamine, and isomers thereof; octylamine, dioctylamine, and isomers thereof; dodecylamine, tetradecylamine, hexadecylamine, octadecylamine, dicyclohexylamine, and isomers thereof; methylenediamine, ethylenediamine, 1,2-diaminopropane, 1,3-diaminopropane, 1,4-diaminobutane, 1,5-diaminopentane, 1,6-diaminohexane, 1,7-diaminoheptane, 1,8-diaminooctane, 1,9-diaminononane, and 1,10-diaminodecane; diethylenetriamine, dipropylenetriamine, triethylenetetramine, tripropylenetetramine, tetraethylenepentamine, tetrapropylenepentamine, pentaethylenehexamine, nonaethylenedecamine, and trimethylhexamethylenediamine; tetra(aminomethyl)methane, tetrakis(2-aminoethylaminomethyl)methane, 1,3-bis(2'-aminoethylamino)propane, triethylene-bis(trimethylene) hexamine, bis(3-aminoethyl)amine, and bishexamethylenetriamine; 1,4-cyclohexanediamine, 4,4'-methylenebiscyclohexylamine, 4,4'-isopropylidenebiscyclohexylamine, norbornadiamine, bis(aminomethyl)cyclohexane, diaminodicyclohexylmethane, isophoronediamine, and menthenediamine; bis(aminoalkyl)benzene, bis(aminoalkyl)naphthalene, bis(cyanoethyl)diethylenetriamine, o-xylylenediamine, m-xylylenediamine, p-xylylenediamine, phenylenediamine, naphthylenediamine, diaminodiphenylmethane, diaminodiethylphenylmethane, 2,2-bis(4-aminophenyl)propane, 4,4'-diaminodiphenyl ether, 4,4'-diaminobenzophenone, 4,4'-diaminodiphenyl ether, 4,4'-diaminodiphenylsulfone, 2,2'-dimethyl-4,4'-diaminodiphenylmethane, 2,4'-diaminobiphenyl, 2,3'-dimethyl-4,4'-diaminobiphenyl, 3,3'-dimethoxy-4,4'-diaminobiphenyl, bis(aminomethyl)naphthalene, and bis(aminoethyl)naphthalene; and N-methylpiperazine, morpholine, 1,4-bis-(8-aminopropyl)-piperazine, piperazine-1,4-diazacycloheptane, 1-(2'-aminoethyl piperazine), 1-[2'-(2"-aminoethylamino)ethyl]piperazine, 1,11-diazacycloeicosane, and 1,15-diazacyclooctacosane. These may be used alone or in combination.

Among those basic catalysts, alkali metal hydroxides are preferred because they enable a high yield of the dialkyl polysulfide (A) and can be separated and removed from a reaction system by a simple procedure, such as distillation and aeration, after the reaction; in particular, sodium hydroxide is more preferred.

The amount of the basic catalyst can be appropriately determined on the basis of the intended reaction rate and is preferably adjusted to be smaller within the range in which reactivity is not impaired; the amount is preferably from 0.05 to 1.0 mass %, and more preferably 0.1 to 0.5 mass % relative to the total mass of the olefin compound (a) and sulfur.

It is preferred that the first process be carried out in the presence of a basic solvent because it can shorten the sulfur chain in the dialkyl polysulfide (A) to be produced and enables efficient production of the dialkyl polysulfide of the present invention. Examples of the basic solvent include cyclic amides, linear amides, and amines.

Examples of the cyclic amides include N-methylpyrrolidone, N-ethylpyrrolidone, N,N-dimethylpropyleneurea, and 1,3-dimethyl-2-imidazolidinone. Examples of the linear amides include N,N-dimethylformamide, dimethylacetamide, diethylformamide, and tetramethylurea. Examples of the amines include triethylamine, pyridine, and tributylamine.

Among the basic solvents, cyclic amides are preferred; in particular, N-methylpyrrolidone is more preferred.

The amount of the basic solvent used in the first process is preferably in the range of 0.5 to 10 mass %, and more preferably 1 to 5 mass % relative to the olefin compound (a).

The content rate of the sulfur to the olefin compound (a) in the first process is as follows: the sulfur content is preferably from 0.5 to 2 mol, and more preferably 0.7 to 1.8 mol relative to 1 mol of the olefin (a) because such content can lower the proportion of polysulfide that is tetra- or higher sulfide in the dialkyl polysulfide (A).

The content rate of the hydrogen sulfide to the olefin compound (a) in the first process is as follows: the hydrogen sulfide content is preferably from 0.3 to 0.8 mol, and more preferably 0.4 to 0.7 mol relative to 1 mol of the olefin (a) because such content enables a reduction in the amount of unreacted olefin in a reaction system in the first process.

In the first process, the reaction temperature at which the 1-olefin compound (a) having a linear end is allowed to react with sulfur in the presence of a hydrogen sulfide is, for example, from 50 to 150° C., and preferably 60 to 130° C.

In the first process, the 1-olefin compound (a) having a linear end is allowed to react with sulfur in the presence of a hydrogen sulfide, and then the reaction system is held at high temperature, so that the amount of dialkyl monosulfide can be effectively reduced. The temperature at which the reaction system is held is preferably in the range of 150 to 250° C., and more preferably 160 to 200° C. The time for which the reaction system is held is preferably from 1 to 72 hours, and more preferably 5 to 48 hours because it can easily make the dialkyl disulfide content be 80% or more.

In the second process, the dialkyl polysulfide (A) obtained in the first process is allowed to react with a sulfide of an alkali metal to decrease the number of sulfur atoms contained in the dialkyl polysulfide (A). This process serves to reduce the number of the sulfur atoms of the sulfur chain of the dialkyl polysulfide (A), thereby producing the dialkyl polysulfide of the present invention.

Examples of the sulfide of an alkali metal include sodium sulfide, potassium sulfide, sodium polysulfide, sodium hydrosulfide, and potassium hydrosulfide. In particular, sodium sulfide is preferred because it has a large effect of reducing the number of the sulfur atoms of the sulfur chain of the dialkyl polysulfide (A) and enables efficient production of the dialkyl polysulfide of the present invention.

The amount of the sulfide of an alkali metal to be used in the second process is preferably in the range of 5 to 50 parts by mass, and more preferably 10 to 45 parts by mass relative to 100 parts by mass of the dialkyl polysulfide (A) because such an amount has a large effect of reducing the number of sulfur atoms of the sulfur chain of the dialkyl polysulfide (A).

Examples of a reaction solvent to be used in the second process include alcohols, cyclic amides, and linear amides. Examples of the alcohols include monoalcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol, and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, and tripropylene glycol; and polyhydric alcohol partial-ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethyl butyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropyleneglycol monomethyl ether, dipropylene glycol monoethyl ether, and dipropylene glycol monopropyl ether.

Examples of the cyclic amides include N-methylpyrrolidone, N-ethylpyrrolidone, N,N-dimethylpropyleneurea, and 1,3-dimethyl-2-imidazolidinone.

Examples of the linear amides include N,N-dimethylformamide, dimethylacetamide, diethylformamide, and tetramethylurea.

Among the above-mentioned solvents, alcohols are preferred because they can promote prompt reaction of the dialkyl polysulfide (A) with a sulfide of an alkali metal to efficiently produce the dialkyl polysulfide of the present invention; in particular, ethylene glycol is more preferred.

Those solvents may be used alone or in combination. Furthermore, the solvent may be used in combination with another solvent for dissolving a sulfide of an alkali metal, e.g. water, a ketone solvent such as acetone, and a polar solvent such as dimethyl sulfoxide.

The amount of the solvent to be used is preferably in the range of 50 to 300 mass %, and more preferably 80 to 250 mass % relative to the mass of a sulfide of an alkali metal.

In the case where the olefin compound (a) is allowed to react with sulfur in the presence of a hydrogen sulfide in a solvent to produce the dialkyl polysulfide (A) in the first process, the dialkyl polysulfide (A) can be collected by a variety of techniques, such as distillation and washing with water, and then can be subjected to a reaction in a proper solvent in the second process.

The temperature of a reaction system in the second process is preferably in the range of 40 to 120° C., and more preferably 50 to 100° C. because it can effectively enhance the disulfide content and trisulfide content and can reduce a side reaction such as decomposition. The reaction time is normally from 1 to 36 hours, and preferably 5 to 24 hours.

It is preferred that a basic compound be used in the reaction system in the second process to extract a by-product to the layer of a reaction solvent, such as an alcohol layer. Examples of the basic compound include sodium hydroxide, potassium hydroxide, calcium hydroxide, barium hydroxide, magnesium hydroxide, and aluminum hydroxide. Among these, sodium hydroxide and potassium hydroxide are preferred because they are highly soluble in alcohol solvents.

The amount of the basic compound to be used is preferably in the range of 0.5 to 20 parts by mass, and more preferably 1 to 10 parts by mass relative to 100 parts by mass of the dialkyl polysulfide (A) in order to maintain the solubility in alcohol solvents.

In the second process, using a sulfide of an alkali metal in combination with a hydrosulfide of an alkali metal enables a by-product to be extracted to the layer of a reaction solvent, such as an alcohol layer, as in using a basic compound in a reaction system. Examples of the hydrosulfide of an alkali metal include sodium hydrosulfide, potassium hydrosulfide, lithium hydrosulfide, rubidium hydrosulfide, and cesium hydrosulfide. In particular, sodium hydrosulfide is preferably used. These hydrosulfides of an alkali metal can be used in the form of a hydrate, an aqueous mixture, an aqueous solution, or an anhydride. Moreover, the hydrosulfide of an alkali metal is more preferably used in combination with a basic compound.

After the second process is completed, a liquid is separated by a routine procedure, and the solid content is removed by filtration, or a volatile component is separated by distillation, thereby being able to obtain the dialkyl polysulfide of the present invention, that is, dialkyl polysulfide in which the total content of a compound in which n in General Formula (1) is 2 and a compound in which n in General Formula (1) is 3 is in the range of 80 to 100 mass % relative to the entire amount of compounds represented by General Formula (1). The content rates of various compounds in which values of n in General Formula (1) are different from each other are determined from the peak areas of charts obtained from high performance liquid chromatography (hereinafter referred to as "HPLC"). HPLC is carried out under the following conditions.

[Conditions of HLPC]

Measurement Equipment: LC-06A manufactured by SHIMADZU CORPORATION

Column: INTERSIL-C8, 4.5 w, 250 mm×4.6 mm

Detector: UV210 nm

Eluent: acetonitrile/water (volume ratio)=85/15, flow rate: 1 ml/min

The extreme pressure additive of the present invention is characterized in that the dialkyl polysulfide of the present invention is used. The extreme pressure additive of the present invention may be composed of only the dialkyl polysulfide of the present invention or may contain another compound that is not the dialkyl polysulfide of the present invention but can be used as an extreme pressure additive. In addition, two or more types of dialkyl polysulfide of the present invention that can be obtained by variously changing the amount of sulfur, a hydrogen sulfide, a sulfide of an alkali metal in the production method of the present invention, or the reaction temperature and the reaction time in the first and second processes may be mixed with each other.

The lubricating fluid composition of the present invention is characterized in that the extreme pressure additive of the present invention and a base oil are used. The base oil is not particularly limited, and a proper base oil can be selected from mineral oils, synthetic oils, and other oils on the basis of the intended use and conditions of use. Examples of the mineral oils include distillate oils obtained by atmospheric distillation of a paraffin-base crude oil, an intermediate base crude oil, or a naphthene base crude oil or by vacuum distillation of the residue after the atmospheric distillation and refined oils obtained by purification thereof, such as solvent refining, hydrogenation refining, dewaxing, and a clay treatment. Examples of the synthetic oils include low molecular weight polybutene; low molecular weight polypropylene; α-olefin oligomers having 8 to 14 carbon atoms and hydrides thereof; polyol esters such as fatty acid esters of trimethylolpropane and fatty acid esters of pentaerythritol; ester compounds such as dibasic acid esters, aromatic polycarboxylic acid esters, and phosphate; alkyl aromatic compounds such as alkylbenzene and alkylnaphthalene; polyglycol oils such as polyalkylene glycol; and silicone oils. These may be appropriately used alone or in combination.

The content rate of the dialkyl polysulfide to the base oil in the lubricating fluid composition of the present invention is not particularly limited; the dialkyl polysulfide content is normally from 0.01 to 50 parts by mass, and preferably 0.05 to 20 parts by mass relative to 100 parts by mass of the base oil.

The lubricating fluid composition of the present invention can further contain a thickener, so that the composition can be used as grease. Examples of a usable thickener include soap-based greases, such as a metal soap-based grease and a complexed soap-based grease, and urea-based greases. In the case where such a thickener is used, it is preferably added to the base oil in advance and evenly mixed therewith.

The lubricating fluid composition may be produced without any limitation provided that the dialkyl polysulfide and the base oil are used; for instance, additives such as oiliness agents, wear resistance agents, extreme pressure agents, other rust-preventive agents, corrosion inhibitors, defoaming agents, detergent dispersants, pour point depressants, viscosity index improvers, antioxidants, emulsifiers, demulsifiers, mold inhibiting agents, friction modifiers, and surfactants may be appropriately used in combination on the basis of the intended applications and performance.

Specific examples of the various additives include the followings: long-chain fatty acids (oleic acid) as oiliness agents; phosphate and dithiophosphate metal salt as wear resistance agents; organic sulfur compounds and organic halogen compounds as extreme pressure agents; carboxylic acids, amines, alcohols, and esters as other rust-preventive agents; nitrogen compounds (e.g., benzotriazole) and sulfur- or nitrogen-containing compounds (e.g., 1,3,4-thiadiazolyl-2,5-bisdialkyldithiocarbamate) as corrosion inhibitors; silicone oils, metal soap, fatty acid esters, and phosphates as defoaming agents; neutral or basic sulfonate, phenate (metal salt type), succinimide, and polymers produced by copolymerization of esters and benzylamine as detergent dispersants; condensates of chlorinated paraffin with naphthalene or phenol, polyalkyl acrylate, polyalkyl methacryalte, polybutene, polyalkyl styrene, and polyvinyl acetate as pour point depressants; polymethacrylate, polyisobutylene, olefin copolymers, and polyalkyl styrene as viscosity index improvers; amine, hindered phenol, zinc thiophosphate, and trialkylphenols as antioxidants; sulfuric acid, sulfonate, phosphate, fatty acid derivatives, amine derivatives, quaternary ammonium salts, and polyoxyethylene-based activators as emulsifiers; quaternary ammonium salts, sulfated oils, and phosphate as demulsifiers; and phenolic compounds, formaldehyde donor compounds, and salicylanilide compounds as mold inhibiting agents.

In the lubricating fluid composition, the dialkyl polyolefin, the base oil, and a thickener and another additive to be optionally used are evenly blended with each other and can be blended by any technique; in this case, heating at a temperature ranging from 30 to 60° C. can be performed for making the mixture even.

The lubricating fluid composition of the present invention can be used in any application; for example, it can be used as a lubricant composition and applied to lubricants used in the driving systems, such as an internal combustion engine, an automatic transmission, a shock absorber, and a power steering, and gears of automobiles; metalworking fluids used for metalworking such as cutting, grinding, and plastic working; and hydraulic oils that are power transmission fluids used for power transmission in hydraulic systems such as hydraulic equipment and machines and for operation such as force control and buffer. In particular, in the case where the lubricating fluid composition of the present invention is employed as a gear oil, it can reduce the degree of swelling with the sealant of a gear box to be used (e.g., chloroprene rubber and nitrile rubber) as compared with typical products; thus, the lubricating fluid composition can be suitably used in applications in which it contacts a sealant.

EXAMPLES

The present invention will now be described further in detail with reference to specific examples. The terms "part" and "%" in Examples are on a mass basis unless otherwise specified.

Example 1 (Preparation of Dialkyl Polysulfide)

Into a 1-liter autoclave having a heater, a hydrogen sulfide inlet, and equipment for absorbing a hydrogen sulfide, 320 g of 1-decene, 73 g of sulfur powder, 0.1 g of a potassium hydroxide, and 4 g of butyl carbitol were put. The autoclave was tightly closed, and then the pressure inside the reaction vessel was reduced to be not more than −0.1 MPa with a vacuum pump for vacuum degassing. Then, heating was carried out to an internal temperature of 120° C. Then, 43 g of hydrogen sulfide gas (purity: 99.9 mol %) was blown thereinto at a pressure of 6 kg/cm$^2$ over 20 hours, and the temperature was subsequently increased to 180° C. and then held for 24 hours. Then, the temperature was decreased to 40° C., a valve connected to the equipment for absorbing a hydrogen sulfide was subsequently opened to return the pressure to normal pressure, air was blown thereinto from an inlet to remove the remaining hydrogen sulfide, thereby obtaining a crude sulfurized olefin. To 430 g of the crude sulfurized olefin, 72 g of ethylene glycol, 73 g of sodium sulfide, and 4 g of sodium hydroxide were added, and a reaction was performed at 60° C. for 10 hours. After the reaction was terminated, an ethylene glycol layer as the lower layer was removed by separation from a liquid in order to obtain a dialkyl polysulfide (1) that was a light yellow upper layer. Table 1 shows the total sulfur content and the active sulfur content in the dialkyl polysulfide (1), the total content of a dialkyl polysulfide in which n in General Formula (1) was 2 and a dialkyl polysulfide in which n in General Formula (1) was 3, and the pyrolysis temperature of the dialkyl polysulfide (1). The pyrolysis temperature was measured under the following conditions.

<Measurement of Pyrolysis Temperature>

Measuring Equipment: Thermogravimetric analyzer manufactured by Rigaku Corporation Rate of Temperature Increase: 20° C./min Example 2 (Same as Above)

A dialkyl polysulfide (2) according to the present invention was produced as in Example 1 except that 249 g of 1-octene was used in place of 320 g of 1-decene. The total sulfur content and the active sulfur content in the dialkyl polysulfide (2), the total content of a dialkyl polysulfide in which n in General Formula (1) was 2 and a dialkyl polysulfide in which n in General Formula (1) was 3, and the pyrolysis temperature of the dialkyl polysulfide (2) were measured as in Example 1. Table 1 shows results of the measurement.

Example 3 (Same as Above)

A dialkyl polysulfide (3) according to the present invention was produced as in Example 1 except that 356 g of 1-dodecene was used in place of 320 g of 1-decene. The total sulfur content and the active sulfur content in the dialkyl polysulfide (3), the total content of a dialkyl polysulfide in which n in General Formula (1) was 2 and a dialkyl polysulfide in which n in General Formula (1) was 3, and the pyrolysis temperature of the dialkyl polysulfide (3) were measured as in Example 1. Table 1 shows results of the measurement.

Example 4 (Same as Above)

A dialkyl polysulfide (4) according to the present invention was produced as in Example 1 except that 409 g of 1-tetradecene was used in place of 320 g of 1-decene. The total sulfur content and the active sulfur content in the dialkyl polysulfide (4), the total content of a dialkyl polysulfide in which n in General Formula (1) was 2 and a dialkyl polysulfide in which n in General Formula (1) was 3, and the pyrolysis temperature of the dialkyl polysulfide (4) were measured as in Example 1. Table 1 shows results of the measurement.

Example 5 (Same as Above)

A dialkyl polysulfide (5) according to the present invention was produced as in Example 1 except that 505 g of LINEALENE 168 manufactured by Idemitsu Kosan Co., Ltd. [mixture of 1-olefins in which alkyl chains [$R^1$—CH($CH_3$)— and $R^2$—CH($CH_3$)—] of compounds represented by General Formula (1) each have 16 to 18 carbon atoms] was used in place of 320 g of 1-decene. The total sulfur content and the active sulfur content in the dialkyl polysulfide (5), the total content of a dialkyl polysulfide in which n in General Formula (1) was 2 and a dialkyl polysulfide in which n in General Formula (1) was 3, and the pyrolysis temperature of the dialkyl polysulfide (5) were measured as in Example 1. Table 1 shows results of the measurement.

Example 6 (Same as Above)

Dialkyl polysulfide (6) of the present invention was produced as in Example 1 except that 320 g of 1-decene was used in combination with 9.1 g of N-methylpyrrolidone. The total sulfur content and the active sulfur content in the dialkyl polysulfide (6), the total content of a dialkyl polysulfide in which n in General Formula (1) was 2 and a dialkyl polysulfide in which n in General Formula (1) was 3, and the pyrolysis temperature of the dialkyl polysulfide (6) were measured as in Example 1. Table 1 shows results of the measurement.

TABLE 1

| | Examples | | | | | |
|---|---|---|---|---|---|---|
| | 1 | 2 | 3 | 4 | 5 | 6 |
| Dialkyl polysulfide | (1) | (2) | (3) | (4) | (5) | (6) |
| 1-olefin used | 1-decene | 1-octene | 1-dodecene | 1-tetradecene | (*1) | 1-decene |
| Total content of compounds in which n in General Formula (1) was 2 or 3 (%) | 87 | 89 | 89 | 87 | 87 | 91 |
| Total sulfur content (%) | 23 | 28 | 21 | 14 | 12 | 21 |
| Active sulfur content (%) | 5 | 5 | 6 | 2 | 1 | 3 |
| Pyrolysis temperature (50%, ° C.) | 272 | 252 | 281 | 287 | 303 | 274 |

Note in Table 1
(*1) LINEALENE 168 manufactured by Idemitsu Kosan Co., Ltd. [mixture of 1-olefins in which the alkyl chains [$R^1$—CH($CH_3$)— and $R^2$—CH($CH_3$)—] of compounds represented by General Formula (1) each have 16 to 18 carbon atoms]

Comparative Example 1

Into a 1-liter autoclave having a heater, a hydrogen sulfide inlet, and equipment for absorbing a hydrogen sulfide, 320 g of 1-decene, 73 g of sulfur powder, 0.1 g of a potassium hydroxide, and 4 g of butyl carbitol were put. The autoclave was tightly closed, and then the pressure inside the reaction vessel was reduced to be not more than −0.1 MPa with a vacuum pump for vacuum degassing. Then, heating was carried out to an internal temperature of 120° C. Then, 43 g of hydrogen sulfide gas (purity: 99.9 mol %) was blown thereinto at a pressure of 6 kg/cm$^2$ over 20 hours, and the temperature was subsequently increased to 180° C. and then held for 24 hours. Then, the temperature was decreased to 40° C., a valve connected to the equipment for absorbing a hydrogen sulfide was subsequently opened to return the pressure to normal pressure, air was blown thereinto from an inlet to remove the remaining hydrogen sulfide, thereby obtaining comparative dialkyl polysulfide (1'). The total sulfur content and the active sulfur content in the comparative dialkyl polysulfide (1'), the total content of a dialkyl polysulfide in which n in General Formula (1) was 2 and a dialkyl polysulfide in which n in General Formula (1) was 3, and the pyrolysis temperature of the comparative dialkyl polysulfide (1') were measured as in Example 1. Table 2 shows results of the measurement.

Comparative Example 2

A dialkyl polysulfide (2') according to the present invention was produced as in Example 1 except that the temperature was immediately decreased to 40° C. without the increase in temperature after the blowing of a hydrogen sulfide. The total sulfur content and the active sulfur content in the dialkyl polysulfide (5), the total content of a dialkyl polysulfide in which n in General Formula (1) was 2 and a dialkyl polysulfide in which n in General Formula (1) was 3, and the pyrolysis temperature of the dialkyl polysulfide (2') were measured as in Example 1. Table 1 shows results of the measurement.

TABLE 2

|  | Comparative Examples | |
| --- | --- | --- |
|  | 1 | 2 |
| Dialkyl polysulfide | (1') | (2') |
| 1-olefin used | 1-decene | 1-decene |
| Total content of compounds in which n in General Formula (1) was 2 or 3 (%) | 43 | 61 |
| Total sulfur content (%) | 25 | 17 |
| Active sulfur content (%) | 12 | 7 |
| Pyrolysis temperature (50%, ° C.) | 260 | 270 |

Example 7 (Lubricating Fluid Composition)

The dialkyl polysulfide (1) was mixed with a mineral oil that has a viscosity of 11 mm$^2$/s at 40° C. such that the dialkyl polysulfide content was 5 mass %, thereby obtaining a lubricating fluid composition (1) of the present invention. The lubricating fluid (1) was used to evaluate corrosiveness to a metal surface and the formability of a film of a metal sulfide on a metal surface in the manners described below. Table 3 shows results of the evaluations.

<Evaluation of Corrosiveness to Metal Surface>

A copper corrosion test was carried out in accordance with JIS K2513, and the state of corrosion on the surface of the copper plate was observed. The test was performed at 100° C. for 3 hours.

<Evaluation of Formability of Film of Metal Sulfide on Metal Surface>

Weld load was measured with a shell four-ball tester in accordance with ASTM D-2783.

Examples 8 to 17

Lubricating fluid compositions (2) to (10) were produced as in Example 7 except that the component contents were adjusted as shown in Tables 3 and 4. The same evaluations as in Example 7 were carried out, and Tables 3 and 4 show results of the evaluations.

Comparative Examples 3 to 8

Comparative lubricating fluid compositions (1') to (6') were produced as in Example 7 except that the component contents were adjusted as shown in Table 5. The same evaluations as in Example 7 were carried out, and Table 5 shows results of the evaluations.

TABLE 3

|  | Examples | | | | | |
| --- | --- | --- | --- | --- | --- | --- |
|  | 7 | 8 | 9 | 10 | 11 | 12 |
| Lubricating fluid composition | (1) | (2) | (3) | (4) | (5) | (6) |
| Dialkyl polysulfide used | (1) | (2) | (3) | (4) | (5) | (6) |
| Dialkyl polysulfide content in mineral oil (mass %) | 5 | 5 | 5 | 5 | 5 | 5 |
| Corrosiveness to metal surface | 1b | 1b | 1b | 1b | 1b | 1b |
| Formability of film of metal sulfide [N(kgf)] | 1617 (165) | 1813 (185) | 1568 (160) | 1568 (160) | 1568 (160) | 1617 (165) |

TABLE 4

|  | Examples | | | | |
| --- | --- | --- | --- | --- | --- |
|  | 13 | 14 | 15 | 16 | 17 |
| Lubricating fluid composition | (6) | (7) | (8) | (9) | (10) |
| Dialkyl polysulfide used | (1) | (1) | (1) | (3) | (3) |
| Dialkyl polysulfide content in mineral oil (mass %) | 1 | 2 | 10 | 1 | 10 |
| Corrosiveness to metal surface | 1b | 1b | 1b | 1b | 1b |
| Formability of film of metal sulfide [N(kgf)] | 1274 (130) | 1421 (145) | 2107 (215) | 1225 (125) | 2058 (210) |

TABLE 5

|  | Comparative Examples | | | | | |
| --- | --- | --- | --- | --- | --- | --- |
|  | 3 | 4 | 5 | 6 | 7 | 8 |
| Lubricating fluid composition | (1') | (2') | (3') | (4') | (5') | (6') |
| Dialkyl polysulfide used | (1') | (1') | (1') | (2') | (2') | (2') |

TABLE 5-continued

| | Comparative Examples | | | | | |
|---|---|---|---|---|---|---|
| | 3 | 4 | 5 | 6 | 7 | 8 |
| Dialkyl polysulfide content in mineral oil (mass %) | 2 | 5 | 10 | 2 | 5 | 10 |
| Corrosiveness to metal surface | 4c | 4c | 4c | 3b | 3b | 4c |
| Formability of film of metal sulfide [N(kgf)] | 1666 (170) | 1862 (190) | 2156 (220) | 1274 (130) | 1470 (150) | 1862 (190) |

The invention claimed is:

1. A dialkyl polysulfide comprising compounds represented by General Formula (1) and produced by a method including a first process in which a 1-olefin compound (a) having a linear end is allowed to react with sulfur in the presence of a hydrogen sulfide to obtain a dialkyl polysulfide (A) and a second process in which the dialkyl polysulfide compound (A) is allowed to react with a sulfide of an alkali metal to reduce the number of sulfur atoms contained in the dialkyl polysulfide (A)

[Chem. 1]

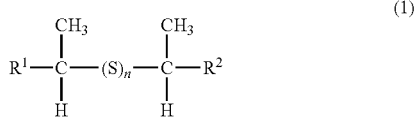

(where $R^1$ and $R^2$ each represent an alkyl group, and n is an integer from 1 to 6), wherein the total content of a compound in which n in General Formula (1) is 2 and a compound in which n in General Formula (1) is 3 is in the range of 80 to 100 mass % relative to the entire amount of the compounds represented by General Formula (1),
wherein the 1-olefin compound (a) having a linear end is at least one selected from the group consisting of 1-butene, 1-pentene, 1-hexene, 1-octene, 1-decene, 1-dodecene, 1-tetradecene, 1-hexadecene, 1-octadecene and 1-eicosene,
wherein the first process includes allowing the 1-olefin compound (a) having a linear end to react with sulfur in the presence of a hydrogen sulfide at 60 to 130° C. and then holding a reaction system at 160 to 200° C. for 5 to 48 hours to obtain the dialkyl polysulfide (A).

2. The dialkyl polysulfide according to claim 1, wherein the total content of a compound in which n in General Formula (1) is 2 and a compound in which n in General Formula (1) is 3 is in the range of 85 to 95 mass % relative to the entire amount of the compounds represented by General Formula (1).

3. An extreme pressure additive comprising the dialkyl polysulfide according to claim 1.

4. A lubricating fluid composition comprising the extreme pressure additive according to claim 3 and a base oil.

5. The lubricating fluid composition according to claim 4, wherein the lubricating fluid composition is used in at least one application selected from the group consisting of a lubricant used for an automobile, a metalworking fluid, and a hydraulic oil.

6. A method for producing a dialkyl polysulfide, the method comprising a first process in which a 1-olefin compound (a) having a linear end is allowed to react with sulfur in the presence of a hydrogen sulfide to obtain a dialkyl polysulfide (A) and a second process in which the dialkyl polysulfide compound (A) is allowed to react with a sulfide of an alkali metal to reduce the number of sulfur atoms contained in the dialkyl polysulfide (A),
wherein the 1-olefin compound (a) having a linear end is at least one selected from the group consisting of 1-butene, 1-pentene, 1-hexene, 1-octene, 1-decene, 1-dodecene, 1-tetradecene, 1-hexadecene, 1-octadecene and 1-eicosene, and
wherein the first process includes allowing the 1-olefin compound (a) having a linear end to react with sulfur in the presence of a hydrogen sulfide at 60 to 130° C. and then holding a reaction system at 160 to 200° C. for 5 to 48 hours to obtain the dialkyl polysulfide (A).

7. The method for producing a dialkyl polysulfide according to claim 6, wherein the first process is carried out in the presence of a basic solvent.

8. The method for producing a dialkyl polysulfide according to claim 6, wherein the second process is carried out in the presence of an alcohol solvent.

9. The method for producing a dialkyl polysulfide according to claim 6, wherein the sulfide of an alkali metal is a sodium sulfide.

10. The method for producing a dialkyl polysulfide according to claim 6, wherein the second process is carried out in the presence of a basic compound.

11. The method for producing a dialkyl polysulfide according to claim 10, wherein the basic compound is a sodium hydroxide.

12. The method for producing a dialkyl polysulfide according to claim 6, wherein the second process is carried out in the presence of a hydrosulfide of an alkali metal.

13. A method for producing a dialkyl polysulfide according to claim 6,
wherein the amount of the basic solvent used in the first process is in the range of 0.5 to 10 mass %, relative to the olefin compound (a).

14. A method for producing a dialkyl polysulfide according to claim 6,
wherein the basic solvent is at least one selected from the group consisting of cyclic amides which includes N-methylpyrrolidone, N-ethylpyrrolidone, N,N-dimethylpropyleneurea, and 1,3-dimethyl-2-imidazolidinone; linear amides which includes N,N-dimethylformamide, dimethylacetamide, diethylformamide, and tetramethylure; and amines which include triethylamine, pyridine, and tributylamine.

15. A method for producing a dialkyl polysulfide according to claim 6,
wherein the basic solvent is N-methylpyrrolidone.

16. A method for producing a lubricating fluid composition, the method comprising a process for obtaining a dialkyl polysulfide containing compounds represented by General Formula (1), the process including a first step in which a 1-olefin compound (a) having a linear end is allowed to react with sulfur in the presence of a hydrogen sulfide to obtain a dialkyl polysulfide (A) and a second step in which the dialkyl polysulfide compound (A) is allowed to react with a sulfide of an alkali metal to reduce the number of sulfur atoms contained in the dialkyl polysulfide (A)

[Chem. 2]

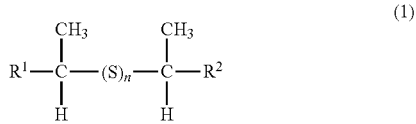

(1)

(where $R^1$ and $R^2$ each represent an alkyl group, and n is an integer from 1 to 6), wherein the total content of a compound in which n in General Formula (1) is 2 and a compound in which n in General Formula (1) is 3 is in the range of 80 to 100 mass % relative to the entire amount of the compounds represented by General Formula (1); and a process for mixing the dialkyl polysulfide with a base oil, wherein the 1-olefin compound (a) having a linear end is at least one selected from the group consisting of 1-butene, 1-pentene, 1-hexene, 1-octene, 1-decene, 1-dodecene, 1-tetradecene, 1-hexadecene, 1-octadecene and 1-eicosene, and wherein the first step includes allowing the 1-olefin compound (a) having a linear end to react with sulfur in the presence of a hydrogen sulfide at 60 to 130° C. and then holding a reaction system at 160 to 200° C. for 5 to 48 hours to obtain the dialkyl polysulfide (A).

17. The method for producing a dialkyl polysulfide according to claim 16, wherein the first process is carried out in the presence of a basic solvent.

18. A method for producing a dialkyl polysulfide according to claim 17, wherein the basic solvent is N-methylpyrrolidone.

* * * * *